United States Patent [19]

Park

[11] Patent Number: 5,682,621
[45] Date of Patent: Nov. 4, 1997

[54] SPORTS SAFETY GLASSES

[75] Inventor: Soo An Park, Seoul, Rep. of Korea

[73] Assignee: Korea OGK Co., Ltd., Seoul, Rep. of Korea

[21] Appl. No.: 621,693

[22] Filed: Mar. 25, 1996

[51] Int. Cl.$^6$ .................................................. A61F 9/02
[52] U.S. Cl. .................................................. 2/441; 2/443
[58] Field of Search ............................... 2/441, 443, 431, 2/432, 426; 351/83, 86, 178

[56] References Cited

U.S. PATENT DOCUMENTS

| | | | |
|---|---|---|---|
| 2,388,205 | 10/1945 | Bernheim et al. | 2/441 |
| 3,081,461 | 3/1963 | Gurtowski | 2/441 |
| 3,122,962 | 3/1964 | De Angelis | 2/441 X |
| 4,556,995 | 12/1985 | Yamamoto. | |
| 4,898,274 | 2/1990 | Patelski, III. | |

FOREIGN PATENT DOCUMENTS 289074  9/1967  Australia ............................... 2/441

*Primary Examiner*—Peter Nerbun
*Attorney, Agent, or Firm*—Robert W. Becker & Associates

[57] ABSTRACT

Sports safety glasses are disclosed having a glasses part with a pair of lenses, frames which the lenses are fit into, foam cushions attached to back sides of the frames, and a band part connected to both ends of the frames of the glasses part. The sports safety glasses include a front outer frame and a rear inner frame to which the foam cushions are attached to come into soft contact with the face; lens mounting faces formed between the front outer frame and rear inner frame to permit the lenses being inserted thereto; and insertion slots formed on one edge of each of the frames and projections mounted on an opposed edge of each frame and fitting into the insertion slots to fasten the frames together.

5 Claims, 3 Drawing Sheets

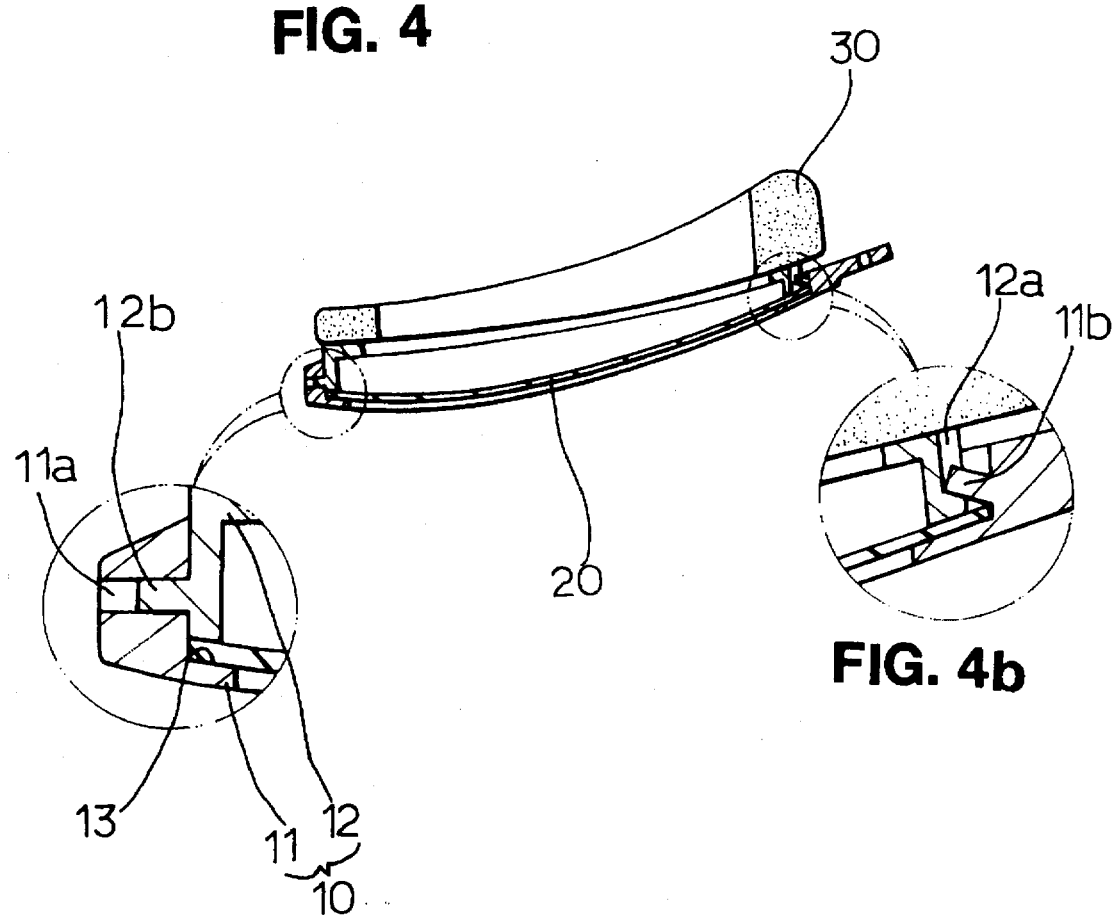

SPORTS SAFETY GLASSES

BACKGROUND OF THE INVENTION

The present invention relates to sports safety glasses that may protect the wearer against sunlight, snow, wind and other dangerous substances such as dust when skiing, bobsledding or snurfing. More particularly, it relates to sorts safety glasses whose lenses can be easily fit into frames and replaced by other ones according to the intensity of sunlight and a wearer's eyesight, taste, etc.

Conventional sports safety glasses include frames 1 made of synthetic resin to have grooves 1a through which lenses 2 are mounted, and foam cushions 3 bonded to the inner back sides of the frames 1 to come in contact with the face of the wearer, which is shown in FIG. 1.

The frames 1 of synthetic resin are heat-treated to be flexible, and the lenses 2 are then inserted into the grooves 1a. As the frames 1 cool down, they harden to set the lenses 2 into the frames 1. After the lenses 2 are combined with the frames 1, the foam cushions 3 are bonded to the inner back sides of the frames 1 by adhesives, which permits a soft and close contact with the face.

Such conventional sports safety glasses do not permit the lenses 2 to be easily fit into or separated from the frames 1, and a wearer cannot replace the lenses 2 of the sports safety glasses once the lenses 2 are fit into the frames 1. However, it is desirable that the lenses 2 be capable of being changed either in color or in shade to the wearer's taste or the intensity of sunlight. Besides, the lenses 2 should be replaced with new ones if they are broken or the wearer's eyesight changes. The conventional safety glasses, however, are not satisfactory on these points, and heating and cooling treatments are applied to their frames and the step for bonding the foam cushions 3 thereto is carried out, whereby the glass manufacturing process becomes complicated.

SUMMARY OF THE INVENTION

The present invention encompasses improvements in sports safety glasses to solve the problems of the conventional sports glasses mentioned above.

Therefore, it is an object of the present invention to provide sports safety glasses whose lenses may be either inserted into or separated from frames in a manner that a wearer may replace them with suitable ones of lenses prepared in various color and shade in response to the intensity of sunlight and his eyesight or taste.

In order to achieve the above object, the presently invented sports safety glasses, with a glasses part having a pair of lenses, frames which the lenses are fit into, foam cushions attached to back sides of the frames, and a band part connected to both ends of the frames of the glasses part, further include a front outer frame and a rear inner frame to which the foam cushions are attached to allow a soft contact with the face; lens mounting faces formed between the front outer frame and rear inner frame to permit the lenses being inserted thereto; and insertion slots formed on one edge of each of the frames and projections mounted on an opposed edge of each frame and fitting in the insertion slots to fasten the frames together.

BRIEF DESCRIPTION OF THE DRAWINGS

The object and advantages of the present invention will appear more clearly from the following specification in conjunction with the accompanying schematic drawings, in which:

FIG. 4 is a transverse sectional view of the sports safety glasses taken along the line A—A of FIG. 2.

FIG. 4a shows a detail of the left edge portion; and

FIG. 4b shows a detail of the right edge portion.

DETAILED DESCRIPTION OF THE INVENTION

A preferred embodiment of the present invention is now described in detail with reference to the accompanying drawings.

Figure 1:
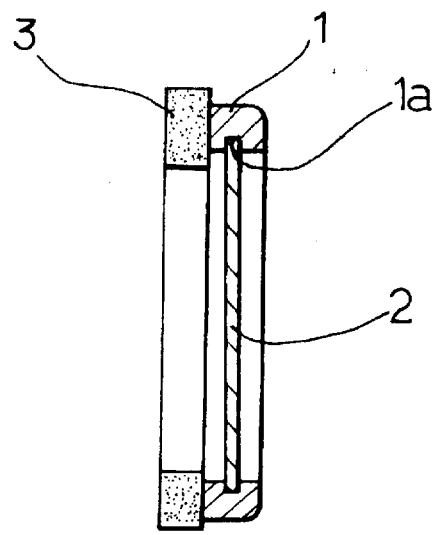
FIG. 1 is a longitudinal sectional view of conventional sports safety glasses.
Figure 2:
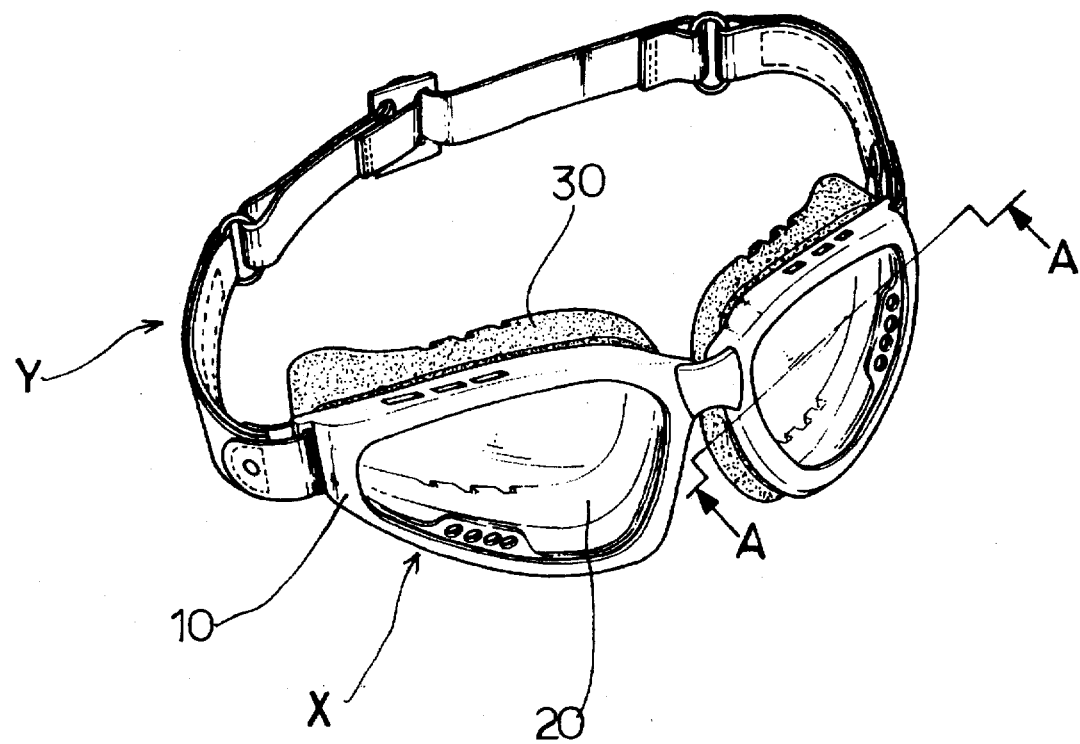
FIG. 2 is a perspective view of sports safety glasses in accordance with a preferred embodiment of the present invention.
Figure 3:
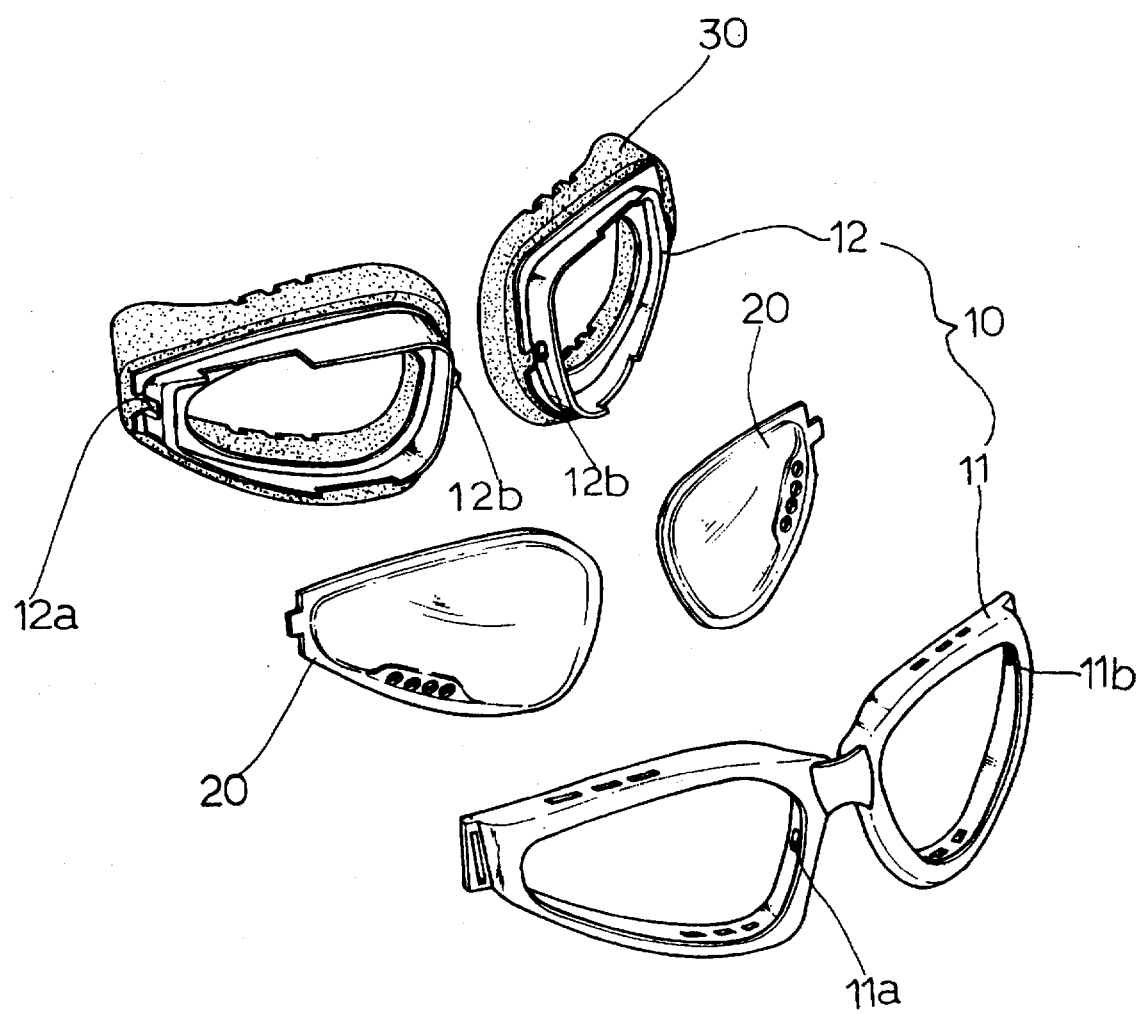
FIG. 3 is an exploded view of a glasses part of the sports safety glasses of FIG. 2.

FIG. 2 is a perspective view of sports safety glasses in accordance with a preferred embodiment of the present invention. FIG. 3 is an exploded perspective view of the sports safety glasses of FIG. 2, and FIG. 4 is a transverse sectional view of the sports safety glasses taken along the line A—A of FIG. 2.

As shown in FIG. 2, the presently invented sports safety glasses have a glasses part X formed of a pair of lenses 20, frames 10 into which the lenses 20 are fit, foam cushions 30 attached to the inner back sides of the frames 10, and a band part Y connected to both ends of the frames 10.

With reference now to FIGS. 3 and 4, the frames 10 of the glasses part X are formed to be divided into a front outer frame 11 and a rear inner frame 12. A lens mounting face 13 is formed between the front outer frame 11 and the rear inner frame 12 so that the lens 20 is placed on the lens mounting face 13. The front outer frame 11 and the rear inner frame 12 are designed to be fastened to each other by means or projections 11b and 12b that are mounted on one edge of each frame 11 and 12 to fit in insertion slots 11a and 12a that are formed on an opposed edge of each frame 11 and 12. The foam cushions 30, which are designed to come into contact with the face of the wearer, are attached to the rear inner frame 12.

Both the front outer frame 11 and rear inner frame 12 are formed of synthetic resin by an injection molding process. The foam cushions 30 are bonded to the rear inner frame 12 prior to fitting the lenses 20 to the frames.

The lenses 20, which can vary in color, diopter and shade, may be selected to the wearer's taste, vision, and environmental conditions at the time of wearing the glasses. The band part Y is connected to both ends of the frames 10 of the glasses part X.

The following description relates to the advantages of the presently invented sports safety glasses from a structural point of view.

The assembly process of the sports safety glasses is as follows.

The lenses 20 are mounted into the lens mounting faces 13 of the front outer frame 11, and the front outer frame 11 is coupled to the rear inner frame 12. At this point, to hold the frames together, the projections 11b and 12b mounted on one edge of each frame are fit into the insertion slots 11a and 12a formed on an opposed edge of each frame respectively. The band part Y is connected to both ends of the frame 10 of the glasses part X in advance, and the foam cushions 30 are previously attached to the inner back side of the rear inner frame 12. Accordingly, the assembly process of the presently invented safety glasses is completed by holding the frames 11 and 12 together.

To replace the lenses 20 with other ones, it is required to separate the front outer frames 11 from the rear inner frame 12. First of all, the projection 11b of the front outer frame 11 is disjoined from the insertion slot 12a of the rear inner frame 12. The projection 12b on the opposed part of the rear inner frame 12 is then pulled out of the insertion slot 11a, thereby completing the separation of the front outer frame 11 from the rear outer frame 12 so that the wearer may replace the lenses 20 with other ones for himself in answer to his need.

The lenses 20 of the sports safety glasses in accordance with the present invention may be replaced with other ones when the wearer wants to change the color of lenses, or when it is preferable to change them in shade to the intensity of sunlight. Besides, the lenses 20 may be substituted with new ones when the eyesight of the wearer changes as well as in case that they are broken.

The present invention has an advantage that a wearer may select suitable lenses provided in various colors and shades in response to his taste and environmental conditions. In addition, the presently invented safety glasses have simplified assembly steps in the manufacture thereof, since it is possible to attach the foam cushions 30 to the rear inner frame 12 and connect the band part Y to both ends of the frames 10 in advance of performing the assembly steps.

Although a presently preferred embodiment of the present invention has been described in detail hereinabove, it should be clearly understood that many variations and/or modifications which may appear to those skilled in the art will still fall within the spirit and scope of the present invention as defined in the appended claims.

What I claim is:

1. Sports safety glasses having a glasses part including frames into which a pair of lenses are fit, with foam cushions being attached to back sides of respective frame portions and a band part being connected to two ends of respective frame portions, said frames each comprising:

a front outer frame;

a rear inner frame that is connectable to said front outer frame and to which each of said foam cushions is attached for contact with the face of a wearer, wherein lens mounting faces are provided for accommodating each of said lenses between said front outer frame and said rear inner frame; and a first projection provided on said front outer frame to be received a first insertion slot of said rear inner frame, and a second projection provided on said rear inner frame to be received in a second insertion slot of said front outer frame, wherein no surface of either projection constitutes a surface of either slot said cooperating first projection and first insertion slot on the one hand and second projection and second insertion slot on the other hand effecting connection of said front outer frame and said rear inner frame to one another.

2. Sports safety glasses according to claim 1, wherein said lens mounting faces are provided on facing surfaces of said front outer frame and said rear inner frame to accommodate said lenses between them.

3. Sports safety glasses according to claim 2, wherein said projections and said insertion slots are disposed adjacent to said lens mounting faces.

4. Sports safety glasses according to claim 1, wherein each part of each of said front outer frame and said rear inner frame that receives a lens is provided with not only one of said first projections or second projections for being respectively received in a cooperating one of said first insertion slots or said second insertion slots, but also with one of said second insertion slots or said first insertion slots for respectively receiving a cooperating one of said second projections or said first projections.

5. Sports safety glasses according to claim 1, wherein said projections and slots of each of said outer frame and said inner frame are completely separate from one another.

* * * * *